(12) United States Patent
Saw (10) Patent No.: US 8,377,432 B2
(45) Date of Patent: Feb. 19, 2013

(54) METHOD AND COMPOSITION FOR NEOCHONDROGENESIS

(76) Inventor: Khay-Yong Saw, Kuala Lumpur (MY)

( * ) Notice: Subject to any disclaimer, the term of this patent is extended or adjusted under 35 U.S.C. 154(b) by 0 days.

(21) Appl. No.: 12/760,083

(22) Filed: Apr. 14, 2010

(65) Prior Publication Data
US 2011/0052526 A1 Mar. 3, 2011

Related U.S. Application Data

(60) Provisional application No. 61/239,200, filed on Sep. 2, 2009.

(51) Int. Cl.
*A61K 9/10* (2006.01)
*C12N 5/0789* (2010.01)

(52) U.S. Cl. .................. 424/93.7; 424/488; 435/372

(58) Field of Classification Search .................. 424/93.7, 424/488; 435/372
See application file for complete search history.

(56) References Cited

U.S. PATENT DOCUMENTS

| | | | |
|---|---|---|---|
| 5,478,739 A | 12/1995 | Slivka et al. |
| 5,842,477 A | 12/1998 | Naughton et al. |
| 6,183,737 B1 | 2/2001 | Zaleske et al. |
| 6,623,963 B1 | 9/2003 | Müller et al. |
| 6,852,330 B2 | 2/2005 | Bowman et al. |
| 6,884,428 B2 | 4/2005 | Binette et al. |
| 7,009,039 B2 | 3/2006 | Yayon et al. |
| 7,104,996 B2 | 9/2006 | Bonutti |
| 7,148,209 B2 | 12/2006 | Hoemann et al. |
| 7,163,563 B2 | 1/2007 | Schwartz et al. |
| 7,192,604 B2 | 3/2007 | Brown et al. |
| 7,201,917 B2 | 4/2007 | Malaviya et al. |
| 7,208,177 B2 | 4/2007 | Geistlich et al. |
| 7,316,822 B2 | 1/2008 | Binette et al. |
| 7,323,445 B2 | 1/2008 | Zhang et al. |
| 7,335,508 B2 | 2/2008 | Yayon et al. |
| 7,361,195 B2 | 4/2008 | Schwartz et al. |
| 7,476,257 B2 | 1/2009 | Sah et al. |
| 7,569,233 B2 | 8/2009 | Malaviya et al. |
| 7,595,062 B2 | 9/2009 | Pedrozo et al. |
| 7,618,451 B2 | 11/2009 | Berez et al. |
| 2002/0082220 A1* | 6/2002 | Hoemann et al. ............... 514/21 |
| 2008/0097606 A1* | 4/2008 | Cragg et al. ............... 623/14.12 |
| 2008/0241250 A1 | 10/2008 | Emans et al. |
| 2009/0123433 A1* | 5/2009 | Shroff .......................... 424/93.7 |
| 2009/0228105 A1 | 9/2009 | Son et al. |

OTHER PUBLICATIONS

Chang et al, J. Orthop. Res. 26:18-26, 2008; available online Aug. 27, 2007.*
Agung et al, Knee Surg. Sports Traum. Arth. 14:1307-1314, 2006.*
Lee et al, Stem Cells 25:2964-2971, 2007.*
Smith et al, Rheumatology 47:1172-1178, 2008; avail. Online Jun. 19, 2008.*
Pless et al, Exp. Hematol. 27:155-161, 1999.*
Tei et al, Stem Cells 26:819-830, 2008; available online Jan. 10, 2008.*
Katayama et al., "The effects of a simplified method for cryopreservation and thawing procedures on peripheral blood stem cells," Bone Marrow Transplantation, 1997, vol. 19, pp. 283-287.
Saw et al., "Articular cartilage regeneration with autologous marrow aspirate and hyaluronic acid: an experimental study in a goat model," Arthroscopy: The Journal of Arthroscopic and Related Surgery, Dec. 2009, vol. 25, No. 12, pp. 1391-1400.
Steadman et al., "Microfracture chondroplasty: indications, treatments, and outcomes," Sports Medicine and Arthroscopy Review, Dec. 2003, vol. 11, No. 4, pp. 236-244.

* cited by examiner

*Primary Examiner* — Kevin K. Hill
(74) *Attorney, Agent, or Firm* — Hamre, Schumann, Mueller & Larson, P.C.

(57) ABSTRACT

A method of neochondrogenesis, where following microfracture surgery or subchondral drilling, includes administering injections of an effective amount of a composition to the damaged, affected connective tissue, for example knee joint cartilage. The composition includes a mixture of hyaluronic acid combined with harvested stem cells, for example autologous peripheral blood-derived stem cells.

9 Claims, 10 Drawing Sheets

Mithoefer predicted values compared with early stem cell clinical data

Fig. 25

One Sample T-Test (Compared to Zero) - ALL cases

| | N | Minimum | Maximum | Mean Statistic | Standard Error | Standard Deviation |
|---|---|---|---|---|---|---|
| Difference | 34 | -29.2 | 56.7 | 12.78 | 3.10 | 18.10 |

| | t | df | Sig. (2-tailed) | Mean Difference | 95% Confidence Interval Lower | Upper |
|---|---|---|---|---|---|---|
| Difference | 4.12 | 33 | 0.0002 | 12.78 | 6.47 | 19.10 | p value = 0.0002

Fig. 26

One Sample T-Test (Compared to Zero) - excluding ACL cases

| | N | Minimum | Maximum | Mean Statistic | Standard Error | Standard Deviation |
|---|---|---|---|---|---|---|
| Difference | 25 | -11.3 | 38.7 | 10.61 | 2.93 | 14.65 |

| | t | df | Sig. (2-tailed) | Mean Difference | 95% Confidence Interval Lower | Upper |
|---|---|---|---|---|---|---|
| Difference | 3.62 | 24 | 0.001 | 10.61 | 4.57 | 16.66 | p value = 0.001

Sample for Peripheral Blood Stem Cells (4 mls)

| Fresh | | Fresh with DMSO | | Frozen | |
|---|---|---|---|---|---|
| CD34+ ($10^6$ cells) | Viability % | CD34+ ($10^6$ cells) | Viability % | CD34+ ($10^6$ cells) | Viability % |
| 4.22 | 99.30 | 2.89 | 92.40 | 5.04 | 83.50 |
| 4.05 | 99.10 | 2.87 | 94.70 | 2.76 | 88.30 |
| 1.73 | 98.80 | 1.38 | 90.40 | 1.18 | 78.60 |
| 3.37 | 98.30 | 2.28 | 92.50 | 2.12 | 81.60 |
| 2.96 | 99.10 | 2.05 | 95.40 | 1.92 | 81.50 |
| 2.3 | 99.30 | 1.64 | 94.40 | 1.42 | 86.80 |
| 1.52 | 98.80 | 1.01 | 91.80 | 0.95 | 84.90 |
| 3.59 | 99.30 | 2.67 | 93.50 | 2.51 | 85.80 |
| 0.93 | 99.40 | 0.50 | 97.60 | 0.44 | 90.90 |
| 7.55 | 99.40 | 5.34 | 87.90 | 4.91 | 73.00 |
| 1.05 | 99.40 | 0.70 | 94.00 | 0.65 | 88.90 |
| 1.68 | 99.20 | 1.21 | 93.20 | 1.03 | 86.20 |
| 0.9 | 98.90 | 0.70 | 94.60 | 0.6 | 86.10 |
| 2.35 | 97.60 | 1.57 | 84.50 | 1.55 | 77.90 |
| 4.73 | 99.00 | 3.72 | 85.00 | 2.99 | 73.50 |
| 1.88 | 98.20 | 1.36 | 88.30 | 1.18 | 80.90 |
| 3.74 | 99.50 | 2.59 | 91.10 | 2.32 | 84.30 |
| 4.87 | 99.40 | 3.47 | 91.40 | 3.02 | 77.90 |
| 0.92 | 99.31 | 0.71 | 93.10 | 0.57 | 91.40 |
| 3.46 | 99.30 | 2.54 | 96.80 | 2.32 | 92.50 |
| Average 2.89 | 99.03 | 2.06 | 92.13 | 1.97 | 83.73 |

Fig. 27

METHOD AND COMPOSITION FOR NEOCHONDROGENESIS

This application claims the benefit of U.S. Provisional Application No. 61/239,200 filed on Sep. 2, 2009, and titled "Method and Composition for Neochondrogenesis", which is herewith incorporated by reference in its entirety.

FIELD

This disclosure relates a method of neochondrogenesis and a composition for the same. More particularly, the disclosure relates to a method of microfracture surgery or subchondral drilling followed by injections of a composition including hyaluronic acid and harvested stem cells, for example peripheral blood-derived stem cells.

BACKGROUND

Hyaline articular cartilage is well known as a specialized avascular tissue composed of chondrocytes embedded in a matrix consisting mainly of Collagen Type II and glycosaminoglycans, such as hyaluronic acid and chondroitin sulphate. Its main function is to allow smooth articulation of weight-bearing joints and to cushion the underlying bone from transmitted compressive and tensile forces involved in joint movement. Hyaline cartilage has an extremely low coefficient of friction for surface to surface contact.

Due to the considerable forces acting, for example on the knee joint, articular cartilage at the knee joint is especially prone to damage from acute trauma as well as from long-term degenerative disease. Owing to its avascular nature, articular cartilage has very limited capacity for repair and partial thickness defects do not heal spontaneously. Full thickness injuries that penetrate the subchondral bone, however, can undergo repair through mobilization of marrow-derived stem cells (MSC) from bone marrow into the blood clot at the site of injury.

Microfracture surgery is well known and takes advantage of this repair mechanism by creating tiny fractures in the subchondral bone through an arthroscopic technique. Subchondral drilling is a variant of microfracture surgery in which a drill, burr or Kirschner wire is used to create drill holes into subchondral bone rather than awls. These procedures are best used in young patients with 80% of those treated showing long term functional improvement. It is believed that microfracture surgery is less useful for lesions more than 15 mm in size, and in older and overweight patients.

The defect is eventually replaced by a hybrid of fibrocartilage and hyaline-like cartilage rather than the original hyaline cartilage. This change can be clearly demonstrated on T2-weighted MRI scans of the knee. The replacement tissue is inferior from a biomechanical standpoint as it is composed mainly of Collagen Type I and seems to be better at resisting tensile forces rather than compressive forces as found in the knee joint. Furthermore, while fibrocartilage does reduce friction when compared to bare bone, it does so to a lesser degree than hyaline cartilage alone. While many patients have shown functional improvement in the first year after surgery, there may be subsequent long term deterioration especially in athletes.

There is significant interest in modifying the basic microfracture technique to see if it is possible to induce formation of replacement hyaline cartilage rather than fibrocartilage. Autologous MSCs cultured in-vitro have been shown to repair full thickness defects, with formation of hyaline cartilage and reconstitution of underlying subchondral bone. Furthermore, the replacement tissue was demonstrated to have superior mechanical properties to normal repair tissue.

The drawbacks of using autologous MSCs are the need for painful bone marrow harvesting and subsequent cell culture which requires specialized facilities. In contrast, autologous peripheral blood-derived stem cells (PSC) are harvested from peripheral blood after stimulation with G-CSF (granulocyte colony stimulating factor) using a technique similar to plasmapheresis. A significant quantity (approximately 100 ml) can be collected in a single session, which can be frozen for future use at a later date for multiple procedures without the need for cell culture.

However, PSCs have limited potential to differentiate into cartilage compared with bone marrow harvested cells. When compared with MSCs, they lack telomerase activity and display significant telomere shortening. In cell culture, PSCs reach their Hayflick limit (i.e. the number of times a cell will divide before it stops due to the telomere reaching a critical length) about 20-25 days after isolation and become senescent. The limited expansion potential of PSCs has safety benefits in that all repair activity should have ceased within a month of the final injection, and should not give long term unexpected side effects like ectopic implantation. Furthermore, the lack of telomerase significantly limits the tumourigenic potential of these cells, which is a latent risk in stem cell therapy.

Other techniques to improve cartilage regeneration have included the use of polymer scaffolds, growth factors, hyaluronic acid, and autologous chondrocyte transplantation, either alone or in combination. Despite the previous studies and methods, improvements to the process of neochondrogenesis can be made.

SUMMARY

A method and composition for neochondrogenesis is described that can provide an improved treatment platform in the repair of one or multiple chondral defects and kissing lesions, for example in cartilage tissue of a knee joint.

Generally, a method of chondrogenesis herein includes, following subchondral drilling into chondral defects for example microfracture surgery, administering post-operative intra-articular injections of stem cells, for example autologous peripheral blood-derived stem cells (PSCs), in combination with hyaluronic acid (HA) in an effective amount to generate new connective tissue.

In one embodiment, a composition for treating chondral defects includes an effective amount of a mixture of autologous peripheral blood-derived stem cells combined with hyaluronic acid. In one embodiment, the composition includes about 8 ml of harvested autologous peripheral blood-derived stem cells and about 2 ml of hyaluronic acid.

The descriptions herein refer to administration of the composition to a knee joint. It will be appreciated, however, that other parts or joints of the body, including connective tissues other than cartilage, may also benefit from the inventive repair methodology and compositions described herein.

DETAILED DESCRIPTION

A method and composition for neochondrogenesis is described that can provide an improved treatment platform in the repair of one or multiple chondral defects and kissing lesions, for example in cartilage tissue of a knee joint. Generally, the method of chondrogenesis herein includes, following subchondral drilling into chondral defects for example microfracture surgery, administering post-operative intra-articular injections of stem cells, for example autologous peripheral blood-derived stem cells (PSCs), in combination with hyaluronic acid (HA) in an effective amount to generate new connective tissue. The composition for treating chondral defects in one embodiment includes an effective amount of a mixture of hyaluronic acid and harvested stem cells, for example autologous peripheral blood-derived stem cells.

While the descriptions herein refer to administration of the composition to a knee joint, it will be appreciated that other parts or joints of the body, including connective tissues other than cartilage, may also benefit from the inventive repair concepts herein.

Applicant has found, through both animal and human clinical studies, that the combination of first performing subchondral drilling followed by administration of harvested stem cells via injection can provide excellent and improved effects in connective tissue repair, e.g. neochondrogenesis. Below is a brief summary of the studies conducted, along with further description and experimental evidence on the human clinical study.

Animal Study

Applicant has studied subchondral drilling combined with intra-articular MSC and hyaluronic acid injections in a goat model. Good results were obtained in the MSC treatment group exhibiting regeneration of hyaline cartilage and restoration of the articular surface. This has been published in the Journal of Arthroscopy (Arthroscopy, The Journal of Arthroscopic and Related Surgery) titled "Articular Cartilage Regeneration with Autologous Marrow-Aspirate and Hyaluronic Acid: An experimental study in a goat model" Volume 25, Issue 12, Pages 1391-1400 (December 2009).

Early Clinical Study

Based on promising results from the animal study, further study was conducted on human subjects. In this study, PSCs were obtained from peripheral blood of the human subject, frozen, and then injected back into the knee joint together with hyaluronic acid after subchondral drilling. Just prior to the injection, the haemarthrosis is aspirated from the operated knee. The actual procedure includes firstly the subchondral drilling, followed by the PSC harvesting at one week after surgery. Right after the harvesting, the first injection of fresh PSC with hyaluronic acid will be given to the patients with the rest of the PSC stored under cryo-preservation. The patients will then be given 4 subsequent injections (PSC+HA) in weekly intervals. Between 4 to 6 months after surgery, booster injection (PSC+HA) may be required. This is administered once per week for 3 weeks. Subsequent booster injection may be injected 4 to 6 months after these initial booster injections. Patients were also subjected to a fixed regime of continuous passive motion therapy and limited to partial weight bearing for a period during post-operation. Follow-up with serial MRI scans showed good repair of the cartilage defects. In selected patients, subsequent second look arthroscopy demonstrated restoration of the smooth articular surface. Biopsy specimens also showed mature hyaline cartilage with normal morphology, and no evidence of degeneration or delamination. All patients had substantial functional improvement after surgery, and there were no significant adverse events related to the procedure.

With further reference to the methods, materials, and overall treatment protocol, the following describes one embodiment of implementing the inventive concepts in the treatment of, for example the cartilage of a human knee. Certain non-limiting details on the surgery performed, the harvesting process, the administration of the composition, post-operative care, and results are described and illustrated.

Generally, the method first includes performing subchondral drilling. Following surgery at day 4, 5 and 6, patients were given a morning dose of 300 micrograms of Filgrastim (G-CSF) subcutaneously. Some patients who wished for a greater harvest with the possibility of contralateral surgery received four doses of Filgrastim. In this scenario, patients received injections on post-surgery days 3, 4, 5, and 6. On post operative day 7, autologous PSC were collected by an automated cell separator (apheresis) utilizing central venous access. The stem cell composition or mixture is prepared, followed by periodic administration. Known post-operative therapy also may be and often is performed.

Microfracture Surgery/Subchondral Drilling

In one embodiment, the microfracture surgical technique employed is adapted from Steadman et al., with curette and arthroscopic awl replaced with subchondral drilling. Subchondral drilling is a variant of microfracture surgery in which a drill, burr or Kirschner wire is used to create drill holes into subchondral bone rather than awls (Steadman, J. R., W. G. Rodkey, and K. K. Briggs, *Microfracture Chondroplasty: Indications, Techniques, and Outcomes*. Sports Med Arthrosc, 2003. 11(4): p. 9). For example, full thickness chondral defects were treated with arthroscopic subchondral drillings. Following surgery, cold therapy is initiated immediately in the post-anesthesia period and continued for the first 24 hours and throughout the first 4 weeks, cryotherapy is utilized for 1 hour, 2 to 3 times per day. On the first day after surgery, the operated knee was placed on Continuous Passive Motion (CPM) therapy for about 2 hours per day for a period of four weeks. CPM therapy is known and can be performed using a variety of therapeutic equipment that provides motion for the knee joint when a subject is on a therapeutic couch for about 2 hours a day. The range of motion is initially set at 0 to 30 degrees and progresses as the clinical situation improves. Additionally, the operated knee is subject to a crutch-assisted partial weight bearing (15 kg partial-weight bearing) for six to eight weeks (patients with femoral-tibia lesion). For patients with drillings to the patello-femoral articulations, they are allowed full weight bearing as tolerated with restrictions from weight bearing on stairs for the first 3 months after surgery. Partial weight bearing is meant as when a subject is walking with crutches, the subject is allowed to put some weight but not full weight on the operated knee.

Harvesting

Human granulocyte colony stimulating factor (G-CSF) is given to mobilize marrow stem cells into peripheral circulation. Following surgery at day 4, 5 and 6, patients were given a morning dose of 300 micrograms of Filgrastim (G-CSF) subcutaneously. Some patients who wished for a greater harvest with the possibility of contralateral knee surgery received four doses of Filgrastim. In this scenario, patients received injections on post-surgery days 3, 4, 5, and 6. Mononuclear cells, for example autologous PSCs are harvested at day 7 after surgery using apheresis. Harvested stem cells are then divided into vials and cryo-preserved for later use. For PSC and MSC, the patient is the source of the stem cells (i.e. autologous stem cells) to provide the safest method and eliminate risks of immune rejection and transmission of blood-borne diseases.

Figure 1:
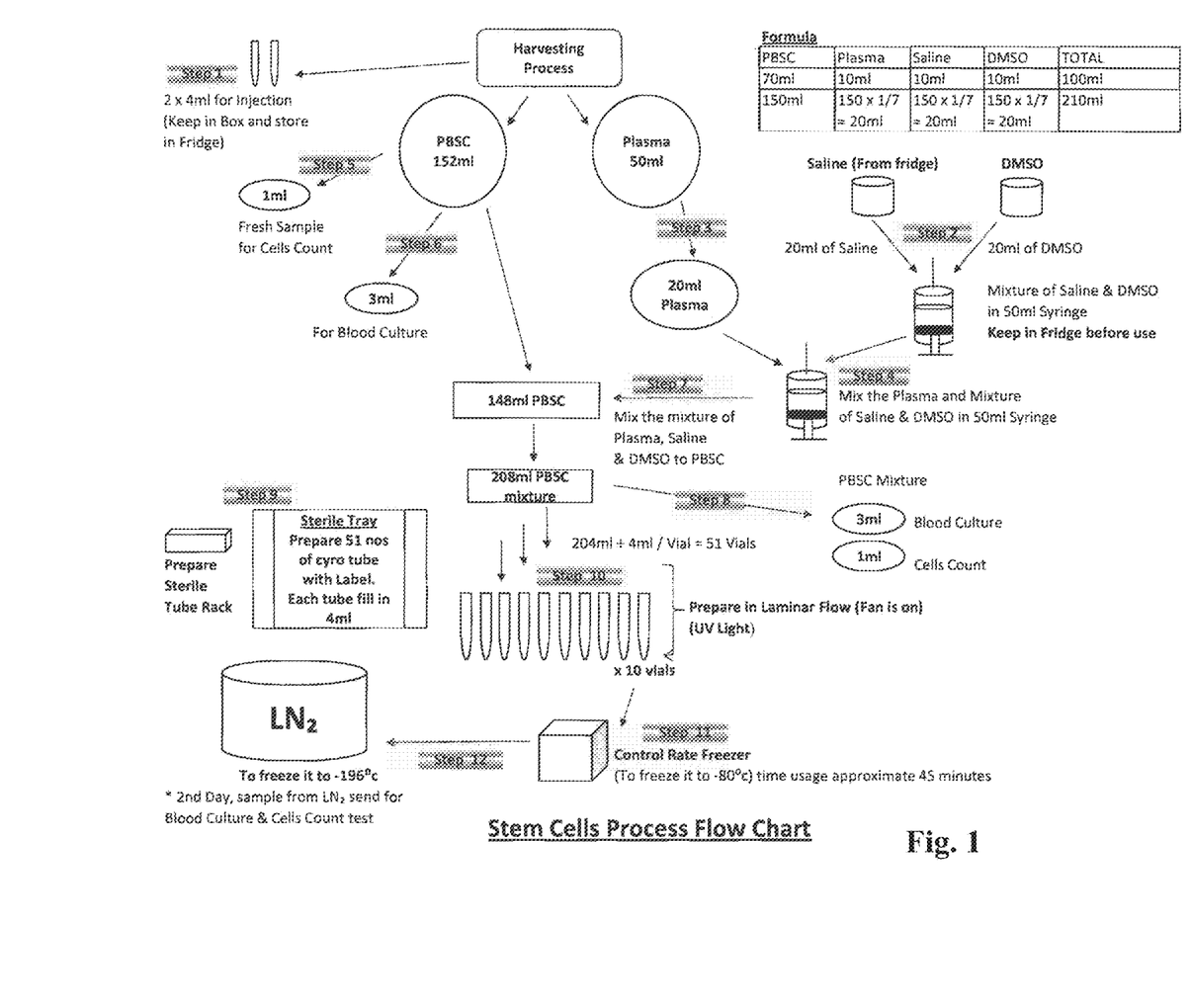
FIG. 1 is a flow chart illustrating the process of stem cell harvesting.

With reference to FIG. 1, one embodiment of a process for stem cell harvesting and storage is illustrated in various steps 1-12. It will be appreciated that the specific volumes employed for the mixtures produced are exemplary only and that the volumes/amounts discussed below can vary as to scale and different volumes/amounts may be employed At step 1, an amount of 2×4 ml of harvested stem cells (e.g. two 4 ml vials), such as peripheral blood stem cells (i.e. PSCs or PBSCs) can be set aside and stored in a refrigerator about 4° C. for more immediate use.

At steps 2 through 7, a storage mixture of saline (cooled from a refrigerator or an ice water bath at about 4° C.), plasma, dimethyl-disulphoxide (DMSO), and PSCs is prepared. For example, in a 100 ml mixture, the following are used: 10 ml of saline; 10 ml of plasma; 10 ml of DMSO; and 70 ml of PSCs. In another example, a 208 ml mixture includes 20 ml of saline, 20 ml of plasma, 20 ml of DMSO, and 148 ml of PSCs (150 ml also may be used for a 210 ml total mixture). More particularly, step 2 shows the mixture of saline with DMSO that is kept in the refrigerator or an ice water bath before use at about 4° C. Step 3 shows obtaining 20 ml of the plasma from the patient's source. Step 4 shows the mixing of the plasma with the mixture of saline and DMSO. Steps 5 and 6 show that, prior to addition of the PSCs to the mixture, about 1 ml of the PSC source (e.g. 152 ml) is taken for a fresh sample cell count and 3 ml of the PSC source is taken for blood culture, which leaves 148 ml of the PSC source. Steps 5 and 6 are quality control steps during the process. Step 7 shows the mixing of the mixture of plasma, saline, and DMSO with the remaining PSC source (e.g. 148 ml).

At step 8, another quality control step can be performed where 1 ml is taken for cell count and 3 ml is taken for blood culture.

At step 9, a sterile tube rack is prepared. In one embodiment, 20 to 80 cryo-tubes or vials are prepared with labelling (sterilised) and each tube/vial is filled with 4 ml of the mixture.

At step 10, the vials are prepared with laminar flow (e.g. Biosafety cabinet Class100 with fan on), where ultraviolet (UV) light has been on for about 1 hour before use. That is, the UV light is turned off during the preparation or filling of the vials, and then the UV light is turned on to resterilize the compartment before using.

At step 11, the vials (e.g. about 20 to 80 vials at a time), are contained in a control rate freezer to about −80° C. for approximately 45 minutes.

At step 12, the vial samples are subject to freezing at −196° C. For example, 2 ml of the vial samples are frozen using liquid nitrogen ($LN_2$), where they can be thawed for later blood culturing and cell count testing. The frozen vials can be thawed, for example, after the second day of freezing. With further reference to FIG. 1, second day means the day after the vials were frozen in liquid nitrogen. For example, if the vials were frozen in liquid nitrogen on Monday, the second day would be Tuesday, at which time the vials can be taken out and thawed, so that the peripheral blood stem cell contents can be sent for blood culture.

To ensure that the vials are prepared and stored in sterile conditions, the following steps may be taken:

a. The cryovials were labeled with printed labels with patient's data.

b. The vials are sterilized to ensure vial and labels are entirely sterile.

c. The caps for the vials are sterilized and packed separately.

d. The pre-labeled sterilized vials are placed in sterile rack for easy and quick aliquots.

e. The sterile caps are screwed on securely and capped prior to control rate freezer stage.

Yield and Viability

Figure 27:
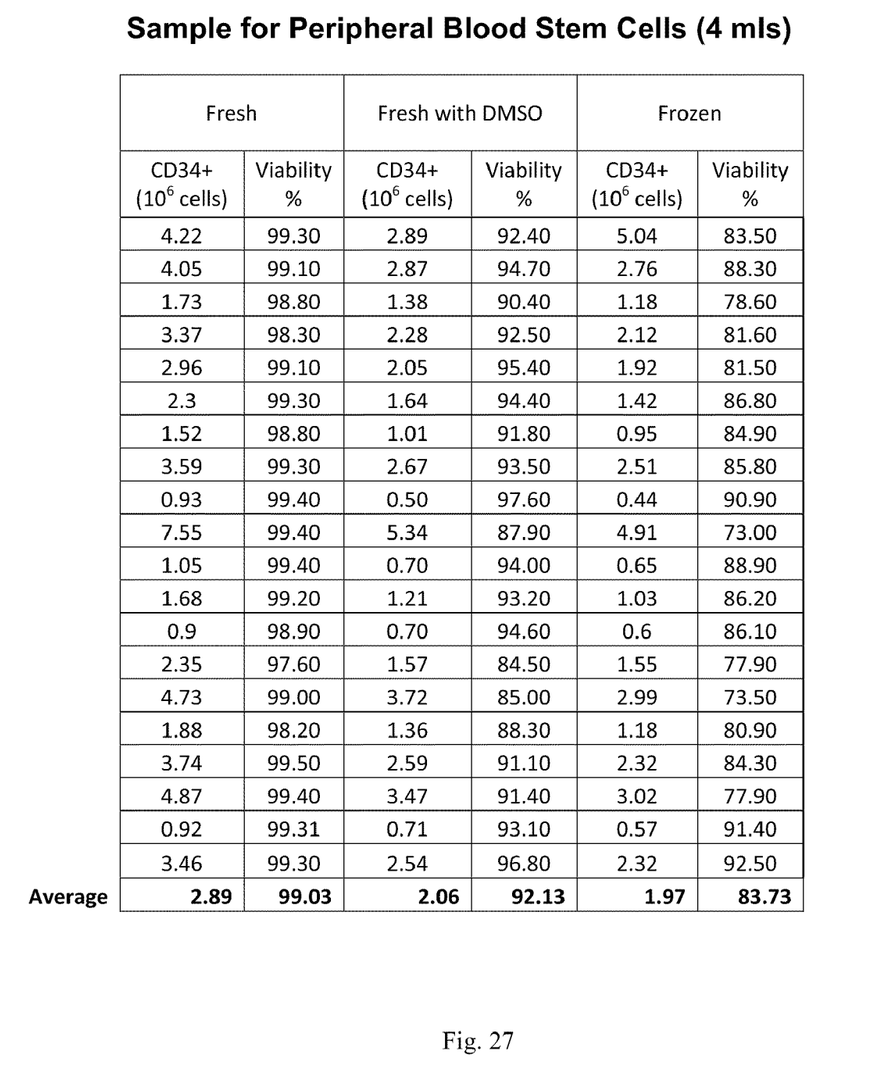
FIG. 27 is a table showing viability of the stem cell samples prepared in accordance with the process of FIG. 1.

FIG. 27 is a table showing viability of the stem cell samples prepared in accordance with the process of FIG. 1. The table in FIG. 27 provides a summary of cell count & yield for the following: fresh samples, fresh samples with DMSO, and post thaw of frozen samples, e.g. produced according to FIG. 1. From literature (Katayama et al, 1997, Bone Marrow Transplantation: 19:page 283-287), the cell viability of known frozen samples is reported to be approximately 80% and fresh samples with DMSO are between 69% to 80%. However, from the improved process disclosed herein it is shown that the samples are far superior with frozen samples, for example having a viability of over 83% on average and with fresh samples (w/DMSO) having a viability of over 92% on average (lowest 84.5%). The results reported in FIG. 27 show that the process of FIG. 1 can provide good viability samples and a further improvement over known viability studies.

Administration

Injections of 2 ml hyaluronic acid+2×4 ml PSC (e.g. two 4 ml vials) are administered, for example by localized injection, on a weekly basis for several weeks, for example a five week duration after surgery started and at the end of the first post-operative week. That is, in Applicant's studies, one week after surgery, a five weekly intra-articular injections of PSCs mixed with 2 mls of HA was commenced.

In one embodiment, about 8 ml of total fresh stem cells is mixed together with 2 ml hyaluronic acid and injected into the patient's knee. On each consecutive week, two 4 ml vials of the stem cell mixture from the cryo-preserved samples is thawed and once again mixed with the same quantity of hyaluronic acid, and injected together into the knee. This is done for a total of five consecutive weeks. Subsequent booster injection may be injected 4 to 6 months after these initial booster injections Thus, in some embodiments, 2×4 ml of stem cells is used if one knee is to be injected (e.g. 8 ml). In the cases of two knees, 2×4 ml of stem cells is used for each knee.

Post-Operative Care

Post-operative care includes wound dressings (about twice a week) and removal of sutures at two weeks after surgery. Physiotherapy with continuous passive motion for 2 hours per day often is conducted on a daily basis for one month after surgery.

The results of the study when applied to certain middle aged human subjects provided the following observations and results.

Interval MRI scans were performed to document chondrogenesis. MRI scans showed satisfactory healing of the subchondral bone and filling-in of the chondral defects suggestive of chondrogenesis.

Second or subsequent-look arthroscopy confirmed tissue regeneration and excellent integration with surrounding articular cartilage.

No evidence of delamination was observed.

Evidence of hyaline cartilage formation was found.

Marked accumulation of proteoglycan was seen in the deeper layers.

Collagen Type I stained and was observed mainly in the superficial layer.

Collagen Type II stained and was observed strongly in the deeper cartilage.

With regard to complications, apart from the discomfort of PSCs harvesting and localized pain associated with the intra-articular injections, there were no other notable adverse reactions.

With reference to FIGS. 2-23, effects on various human patient examples employing the inventive concepts herein are illustrated.

Figure 2:
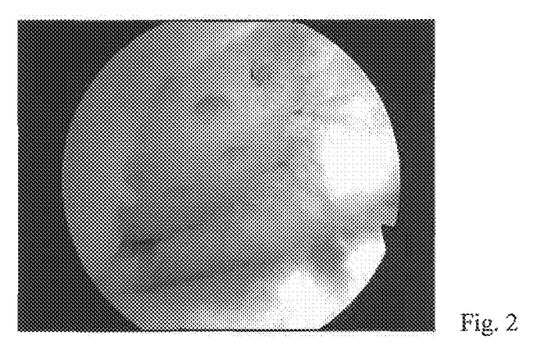
FIG. 2 is a photograph of a human patient's lateral femoral condyle at intra-operation that shows the chondral defect.
Figure 3:
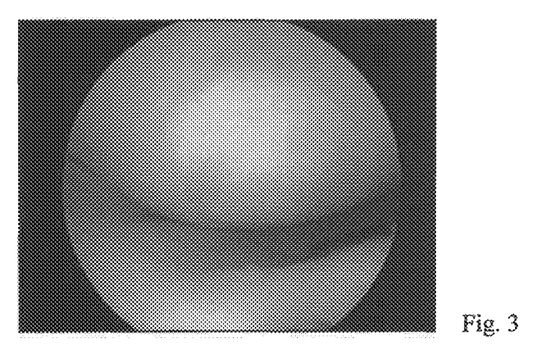
FIG. 3 is a photograph of the human patient's lateral femoral condyle in FIG. 2 at one year post-operation that shows the regenerated cartilage.
Figure 4:
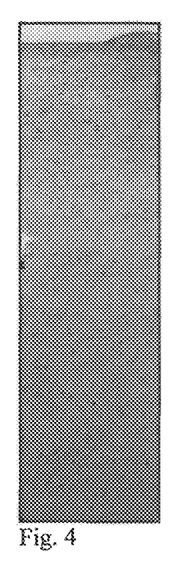
FIG. 4 is a photograph of a biopsy from a sample taken from the human patient's lateral femoral condyle in FIG. 3 (one year post-operation) that shows results from a hematoxylin and eosin (H&E) stain.
Figure 5:
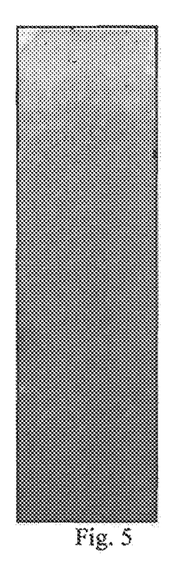
FIG. 5 is a photograph of a biopsy from a sample taken from the human patient's lateral femoral condyle in FIG. 3 (one year post-operation) that shows results from a Safranin-O stain.
Figure 6:
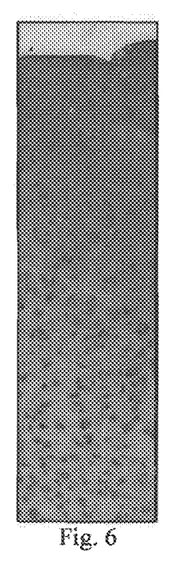
FIG. 6 is a photograph of a biopsy from a sample taken from the human patient's lateral femoral condyle in FIG. 3 (one year post-operation) that shows Collagen Type I results.
Figure 7:
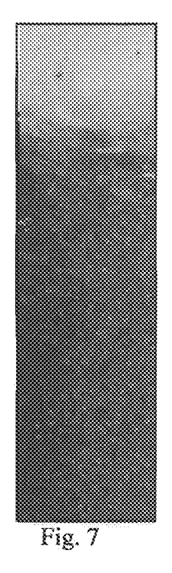
FIG. 7 is a photograph of a biopsy from a sample taken from the human patient's lateral femoral condyle in FIG. 3 (one year post-operation) that shows Collagen Type II results.

FIGS. 2-9 show progress and results from treatment on a lateral femoral condyle of a 55 year old female patient using the concepts herein. Particularly, FIG. 2 is a photograph of the patient's lateral femoral condyle at intra-operation and shows the chondral defect. FIG. 3 is a photograph of the patient's lateral femoral condyle at one year post-operation and shows the regenerated cartilage. FIG. 4 is a photograph of a biopsy from a sample taken from the patient's lateral femoral condyle (at one year post-operation) and shows results from a hematoxylin and eosin (H&E) stain. FIG. 5 is a photograph of a biopsy from a sample taken from the patient's lateral femoral condyle (at one year post-operation) and shows results from a Safranin-O stain. FIGS. 6 and 7 are photographs of biopsies from samples taken from the patient's lateral femoral condyle (at one year post-operation) that show Collagen Type I and Type II results. The biopsy specimens show mature hyaline cartilage with normal morphology, and no evidence of degeneration or delamination. All patients had substantial functional improvement after surgery, and there were no significant adverse events related to the procedure.

Figure 8:
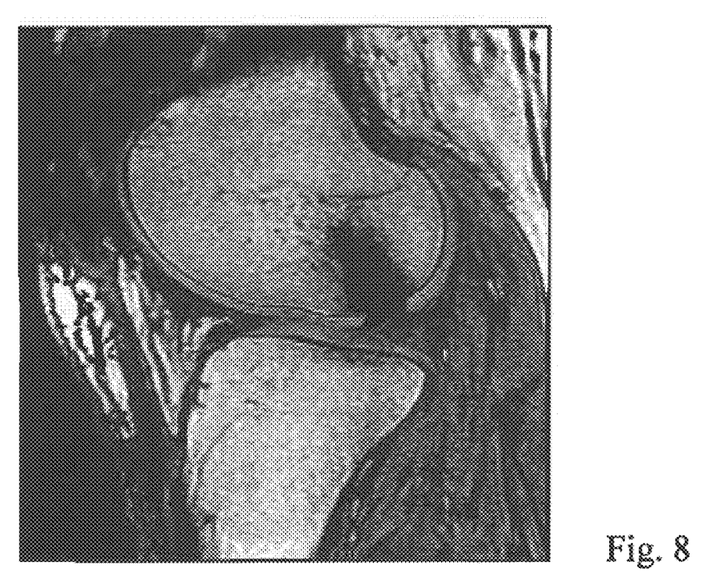
FIG. 8 is a magnetic resonance image of the human patient's lateral femoral condyle in FIG. 2 but soon after post-operation.
Figure 9:
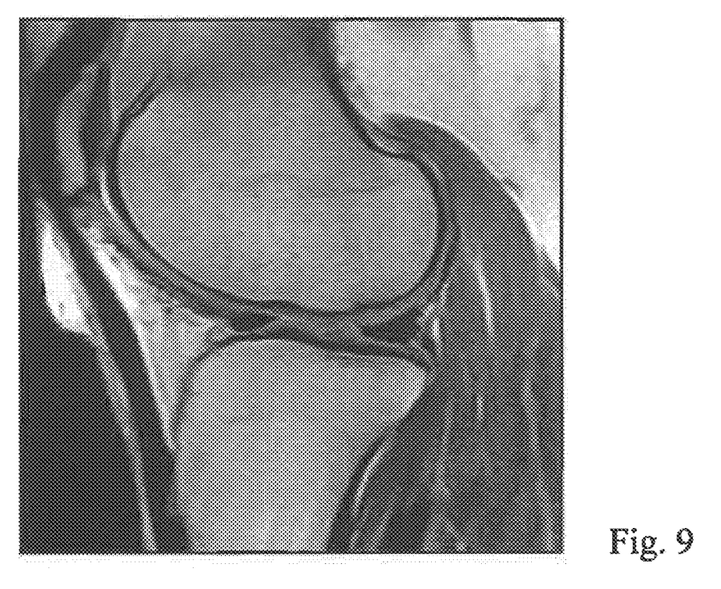
FIG. 9 is a magnetic resonance image of the human patient's lateral femoral condyle in FIG. 3 (one year post-operation) that shows the regenerated cartilage.

FIG. 8 is a magnetic resonance image of the patient's lateral femoral condyle but soon after post-operation. FIG. 9 is a magnetic resonance image of the patient's lateral femoral condyle (at one year post-operation) and shows the regenerated cartilage.

Figure 10:
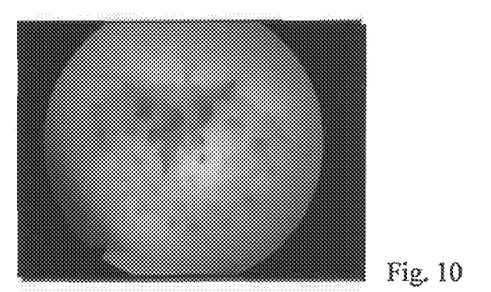
FIG. 10 is a photograph of a human patient's lateral patella facet at intra-operation that shows the chondral defect.
Figure 11:
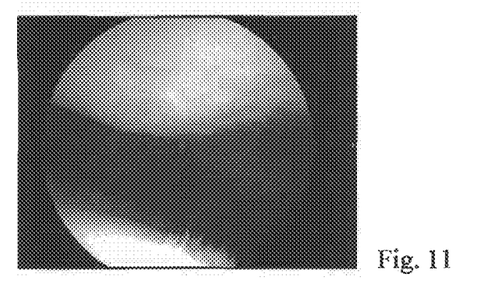
FIG. 11 is a photograph of the human patient's lateral patella facet in FIG. 10 at ten months post-operation that shows the regenerated cartilage.
Figure 12:
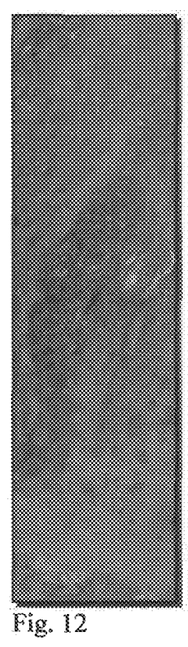
FIG. 12 is a photograph of a biopsy from a sample taken from the human patient's lateral patella facet in FIG. 11 (ten months post-operation) that shows results from a hematoxylin and eosin (H&E) stain.
Figure 13:
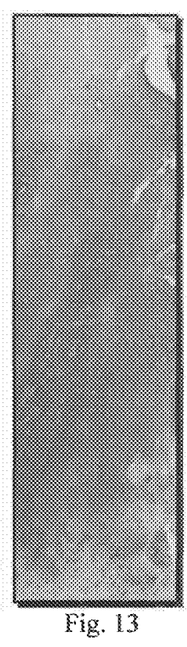
FIG. 13 is a photograph of a biopsy from a sample taken from the human patient's lateral patella facet in FIG. 11 (ten months post-operation) that shows results from a Safranin-O stain.
Figure 14:
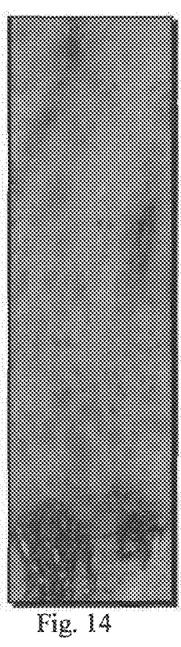
FIG. 14 is a photograph of a biopsy from a sample taken from the human patient's lateral patella facet in FIG. 11 (ten months post-operation) that shows Collagen Type I results.
Figure 15:
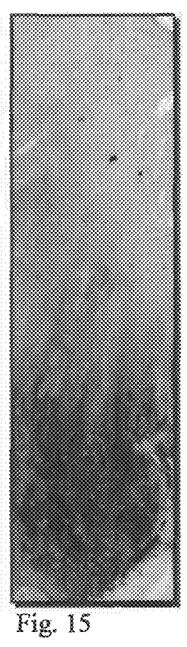
FIG. 15 is a photograph of a biopsy from a sample taken from the human patient's lateral patella facet in FIG. 11 (ten months post-operation) that shows Collagen Type II results.

FIGS. 10-19 show progress and results from treatment on a lateral patella facet of a 43 year old female patient using the concepts herein. Particularly, FIG. 10 is a photograph of the patient's lateral patella facet at intra-operation and shows the chondral defect. FIG. 11 is a photograph of the patient's lateral patella facet at ten months post-operation and shows the regenerated cartilage. FIG. 12 is a photograph of a biopsy from a sample taken from the patient's lateral patella facet (at ten months post-operation) and shows results from a hematoxylin and eosin (H&E) stain. FIG. 13 is a photograph of a biopsy from a sample taken from the patient's lateral patella facet (at ten months post-operation) and shows results from a Safranin-O stain. FIGS. 14 and 15 are photographs of biopsies from samples taken from the patient's lateral patella facet (at ten months post-operation) and show Collagen Type I and Type II results. The biopsy specimens show mature hyaline cartilage with normal morphology, and no evidence of degeneration or delamination. All patients had substantial functional improvement after surgery, and there were no significant adverse events related to the procedure.

Figure 16:
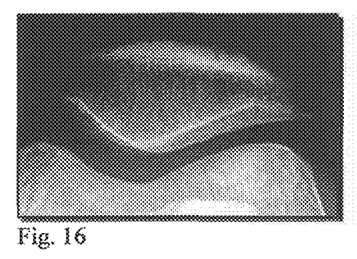
FIG. 16 is an x-ray image of the human patient's lateral patella facet in FIG. 10 but shown at a pre-operation.
Figure 17:
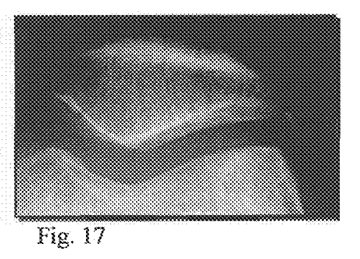
FIG. 17 is an x-ray image of the human patient's lateral patella facet in FIG. 11 and shown at ten months post-operation.
Figure 18:
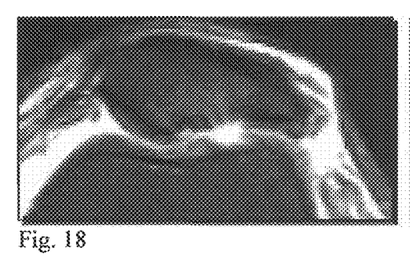
FIG. 18 is a magnetic resonance image of the human patient's lateral patella facet in FIG. 10 but soon after post-operation.
Figure 19:
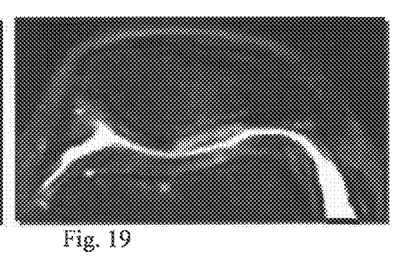
FIG. 19 is a magnetic resonance image of the human patient's lateral patella facet in FIG. 11 (ten months post-operation) that shows the regenerated cartilage.

FIG. 16 is an x-ray image of the patient's lateral patella facet but shown at pre-operation. FIG. 17 is an x-ray image of the patient's lateral patella facet shown at ten months post-operation. FIG. 18 is a magnetic resonance image of the human patient's lateral patella facet in FIG. 10 but soon after post-operation. FIG. 19 is a magnetic resonance image of the patient's lateral patella facet (at ten months post-operation) showing the regenerated cartilage.

Figure 20:
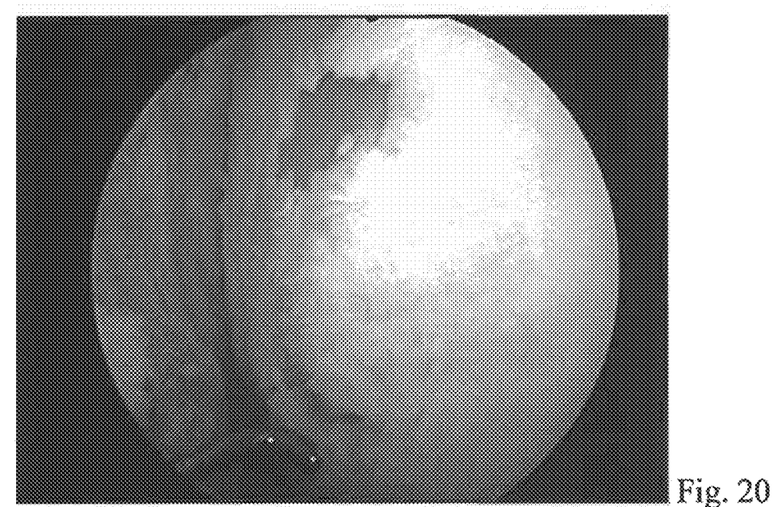
FIG. 20 is a photograph of a human patient's medial femoral condyle at intra-operation and showing a kissing legion at the medial compartment.
Figure 21:
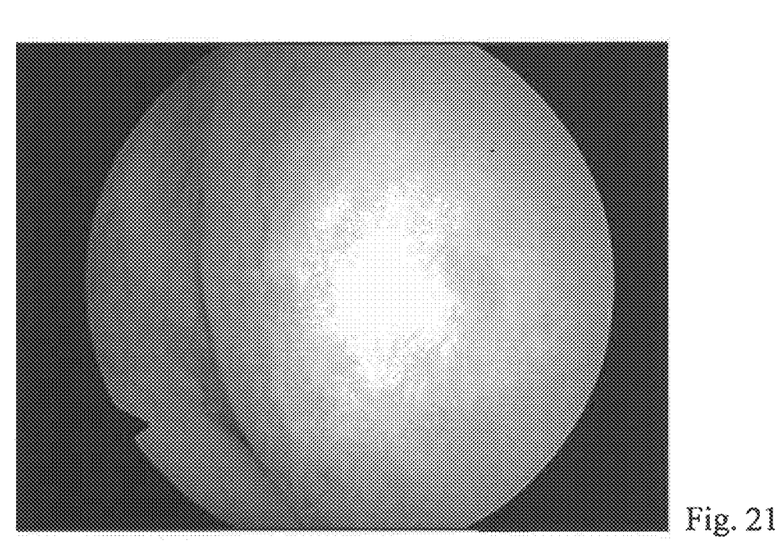
FIG. 21 is a photograph of the human patient's medial femoral condyle but at eight months post-operation and shows regenerated cartilage.
Figure 22:
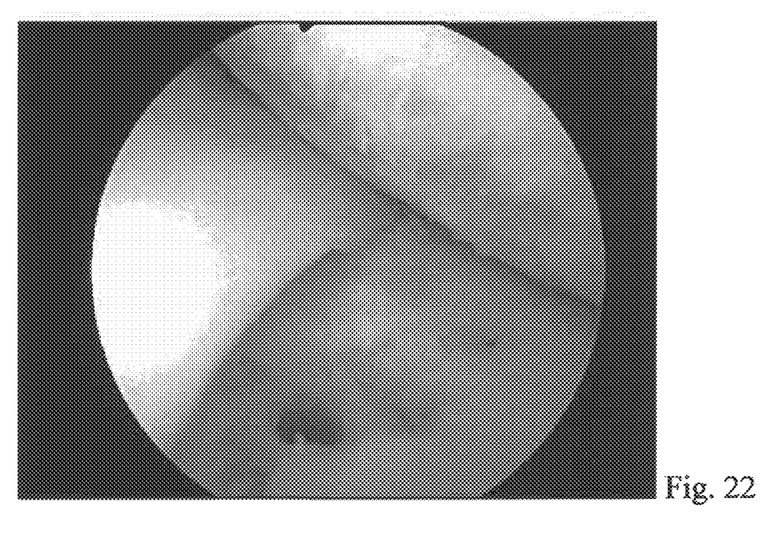
FIG. 22 is a photograph of a human patient's medial tibial plateau at intra-operation and showing a kissing legion at the medial compartment.
Figure 23:
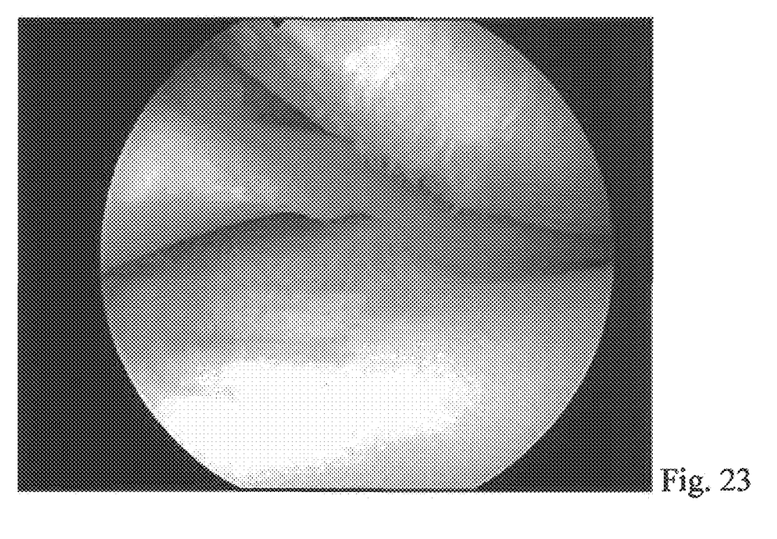
FIG. 23 is a photograph of the human patient's medial tibial plateau but at eight months post-operation and shows regenerated cartilage.

FIGS. 20-23 show results using the concepts herein from treatment on a kissing lesion on the medial compartment of a 49 year old female patient, particularly on the medial femoral condyle and medial tibial plateau. FIG. 20 is a photograph of a human patient's medial femoral condyle at intra-operation and showing a kissing lesion at the medial compartment. FIG. 21 is a photograph of the patient's medial femoral condyle but at eight months post-operation and shows regenerated cartilage. FIG. 22 is a photograph of a human patient's medial tibial plateau at intra-operation and showing a kissing lesion at the medial compartment. FIG. 23 is a photograph of the patient's medial tibial plateau but at eight months post-operation and shows regenerated cartilage.

Figure 24:
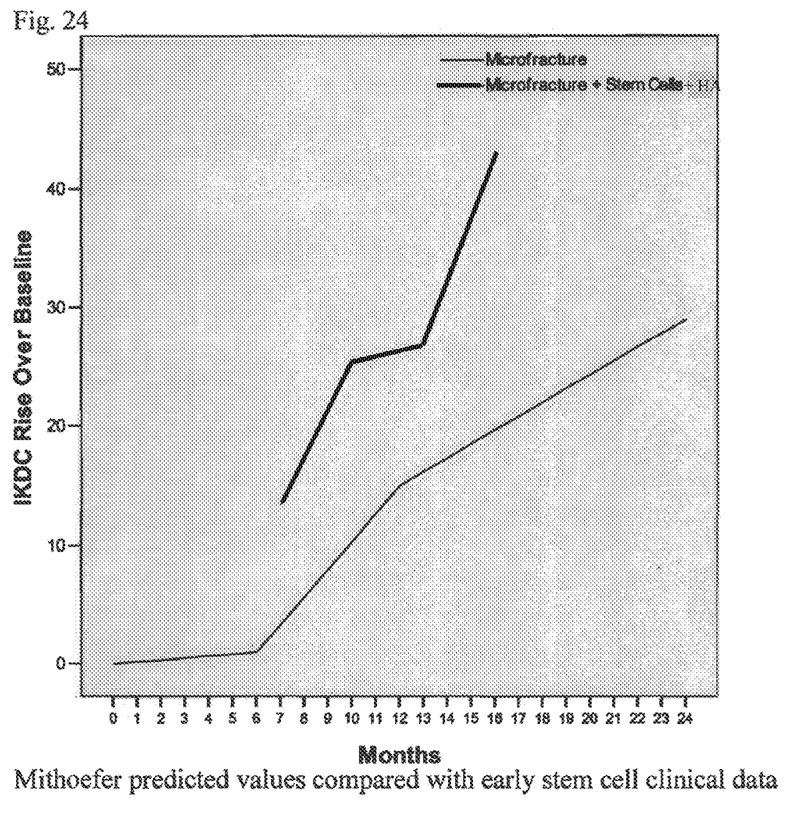
FIG. 24 is a graph showing a comparison of International Knee Documentation Committee (IKDC) scores for the microfracture surgery alone against the combined method of microfracture surgery and stem cells.
Figure 25:
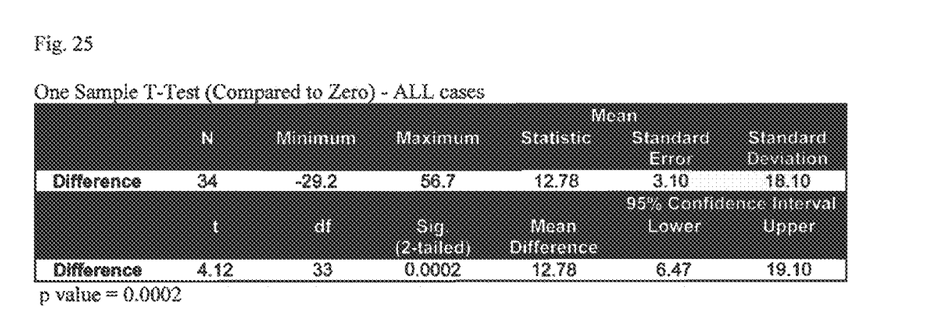
FIG. 25 is a table that shows sample clinical test results.
Figure 26:
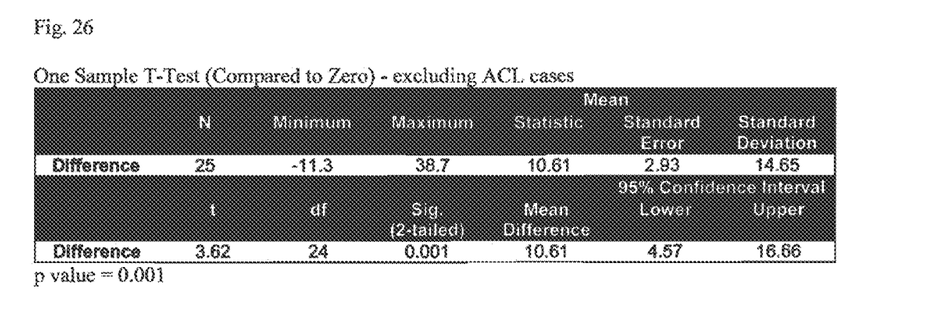
FIG. 26 is another table that shows sample clinical test results.

With further reference to additional results, FIGS. 24-26 show additional data on the effects of using the stem cell composition. FIG. 24 is a graph showing a comparison of International Knee Documentation Committee (IKDC) scores for the microfracture surgery alone against the combined method of microfracture surgery and treatment with stem cells mixed with HA. As illustrated, the use of microfracture surgery along with stem cells provides higher values of IKDC scores.

FIGS. 25 and 26 are tables that show sample clinical results based on statistical t-tests. More particularly, FIGS. 25 and 26 refer to the type of operative cases that were performed using the methods herein. For example, FIG. 26 excluded cases that involved anterior cruciate ligament (ACL) reconstruction, because of the way the IKDC scoring is reported, instability itself has a score as a patient with an ACL deficiency has instability before surgery, which may show a larger amount of improvement following surgery.

The methods and compositions herein provide clinically relevant and advantages in neochondrogenesis. The process herein involves, following a single arthroscopic procedure (e.g. microfracture surgery or subchondral drilling), post-operative intra-articular injections of autologous stem cells (e.g. PSCs) in combination with HA. The methods and compositions herein can help repair one or multiple and kissing lesions and other chondral defects.

The embodiments disclosed in this application are to be considered in all respects as illustrative and not limitative. The scope of the invention is indicated by the appended claims rather than by the foregoing description; and all changes which come within the meaning and range of equivalency of the claims are intended to be embraced therein.

What is claimed is:

1. A method of neochondrogenesis comprising:
    (1) performing an arthroscopic procedure on a joint of a human patient in need of neochondrogenesis;
    (2) at about 3 to 4 days after performing the arthroscopic procedure in (1), administering a granulocyte colony-stimulating factor to the human patient; and
    (3) at about a week after performing the arthroscopic procedure in (2), injecting into the joint of the human patient, a composition that includes a combination of autologous peripheral blood-derived stem cells that are positive for CD34 and hyaluronic acid in an amount sufficient for generating and repairing articular cartilage tissue of the joint.

2. The method of claim 1, wherein in (2), the granulocyte colony-stimulating factor is injected daily for about 3 to 4 days, and the granulocyte colony-stimulating factor is injected prior to injecting the composition in (3).

3. The method of claim 1, wherein the arthroscopic procedure includes subchondral drilling.

4. The method of claim 1, wherein the arthroscopic procedure includes performing a microfracture surgical procedure.

5. The method of claim 1, wherein in (3), the composition is injected on a weekly basis.

6. The method of claim 1, wherein in (3), the composition is injected on a weekly basis for five weeks.

7. The method of claim 1, wherein the composition in (3) includes about $1 \times 10^6$ to about $8 \times 10^6$ autologous peripheral blood-derived stem cells per about 2 ml of hyaluronic acid.

8. The method of claim 1, wherein in (3), the articular cartilage tissue is generated and repaired at an area of the human patient having a chondral defect or a kissing lesion.

9. The method of claim 1, wherein in (3), the articular cartilage tissue is generated at a knee joint.

* * * * *